US005894981A

United States Patent [19]
Kelly

[11] Patent Number: 5,894,981
[45] Date of Patent: Apr. 20, 1999

[54] INTEGRATED PULL TESTER WITH AN ULTRASONIC WIRE BONDER

[75] Inventor: Gregg S. Kelly, Newport Beach, Calif.

[73] Assignee: Orthodyne Electronics Corporation, Irvine, Calif.

[21] Appl. No.: 08/757,877

[22] Filed: Nov. 27, 1996

[51] Int. Cl.[6] .................................................. H01L 21/60
[52] U.S. Cl. .................... 228/104; 228/180.5; 73/827
[58] Field of Search .................................. 228/103, 104, 228/110.1, 180.5; 73/827, 828

[56] References Cited

U.S. PATENT DOCUMENTS

| | | |
|---|---|---|
| 3,572,108 | 3/1971 | McShane et al. . |
| 3,840,169 | 10/1974 | Steranko ........................ 228/4.5 |
| 3,890,831 | 6/1975 | Cusick et al. . |
| 3,945,248 | 3/1976 | West . |
| 4,415,115 | 11/1983 | James ........................... 228/4.5 |
| 4,418,858 | 12/1983 | Miller ........................... 228/4.5 |
| 4,558,596 | 12/1985 | McBrearty et al. ............ 228/4.5 |
| 4,674,671 | 6/1987 | Fister et al. ................... 228/111 |
| 4,786,860 | 11/1988 | Zimmerman .................. 228/4.5 |
| 4,815,001 | 3/1989 | Uthe et al. .................... 228/103 |
| 4,895,028 | 1/1990 | Mayer . |
| 5,111,989 | 5/1992 | Holdgrafer et al. ........... 228/180.5 |
| 5,326,015 | 7/1994 | Weaver ......................... 228/4.5 |
| 5,402,927 | 4/1995 | Frasch .......................... 228/4.5 |
| 5,591,920 | 1/1997 | Price ............................. 228/4.5 |

*Primary Examiner*—Samuel M. Heinrich
*Attorney, Agent, or Firm*—George F. Bethel; Patience K. Bethel

[57] ABSTRACT

An ultrasonic wire bonder including apparatus for testing a bond includes a bonding tool ultrasonically driven for welding a wire on an underlying substrate and a clamp for holding the wire to be bonded by the bonding tool. The same clamp or other pulling apparatus moves the wire that has been bonded with a pre-established force to determine whether the bond will withstand the force. The accompanying method for testing a bond includes holding the wire after the bond has been made with the same holder and pulling the wire with a pre-established force substantially along the direction of the wire's longitudinal axis to determine the strength of the bond.

24 Claims, 7 Drawing Sheets

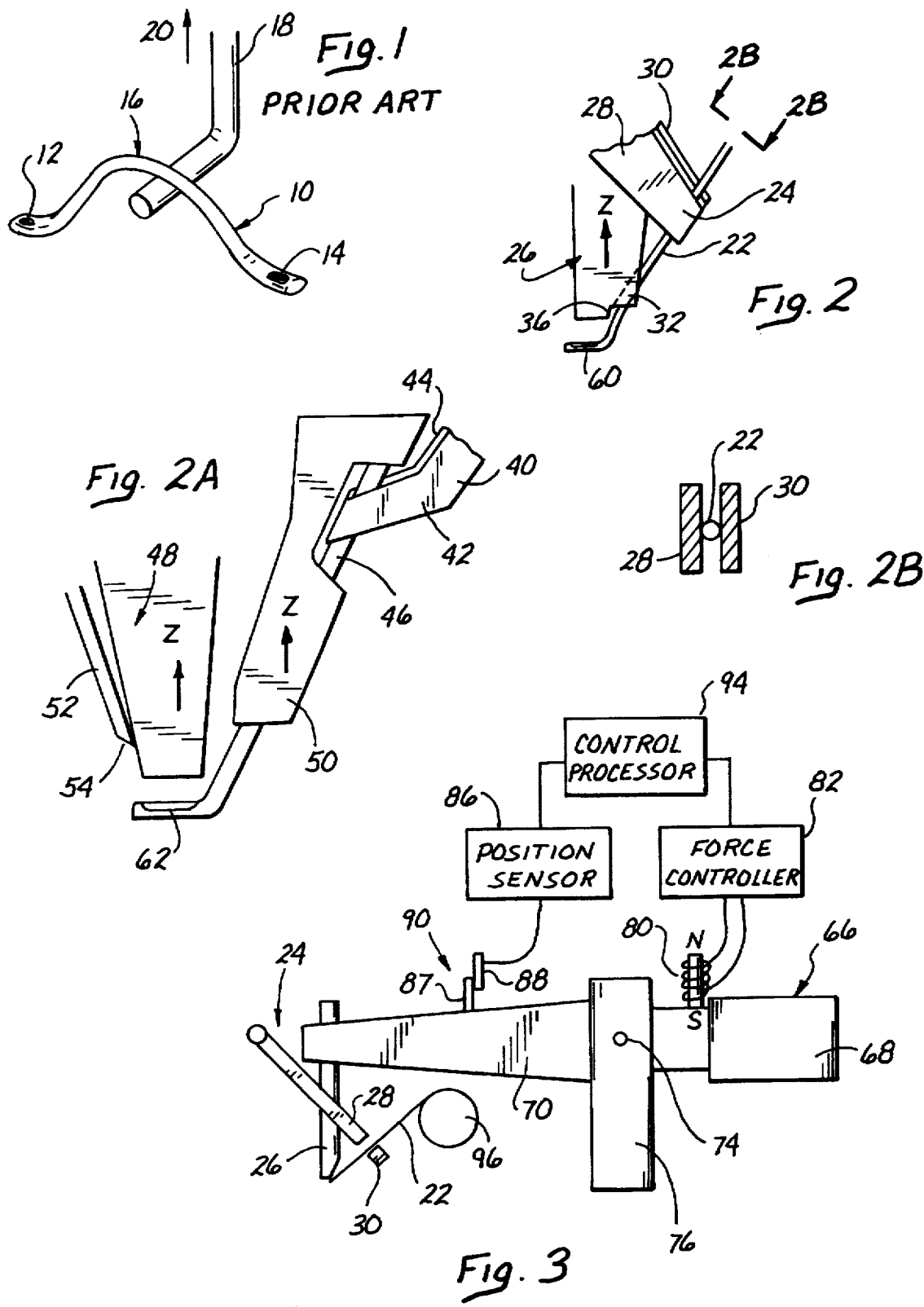

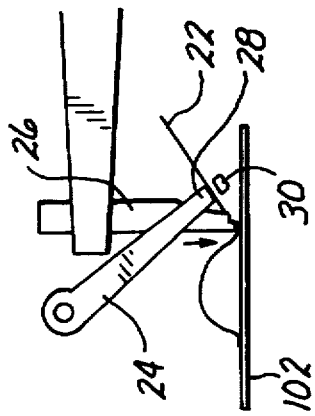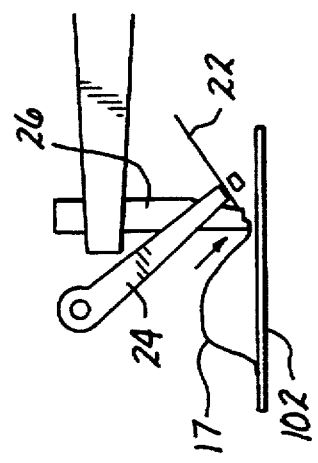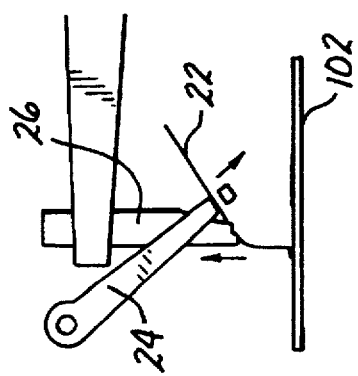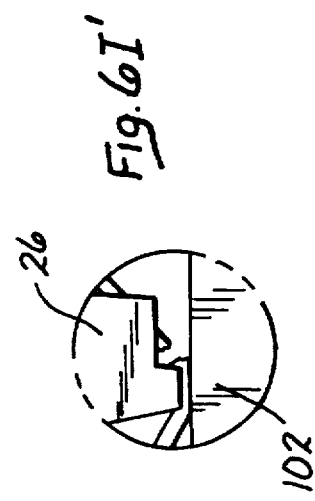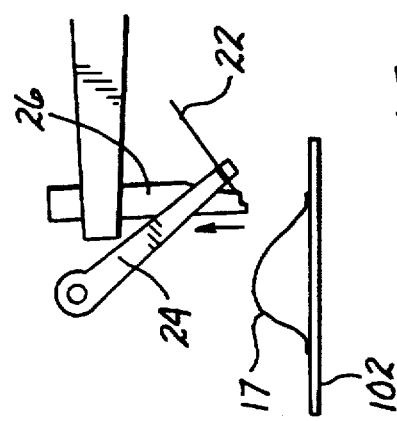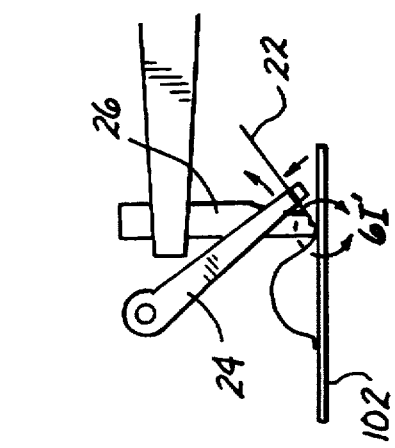

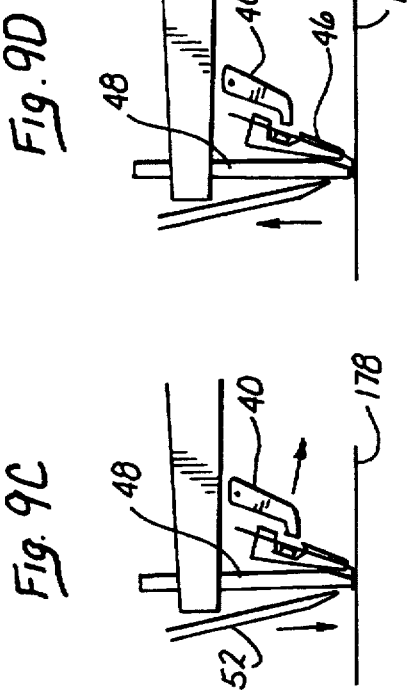
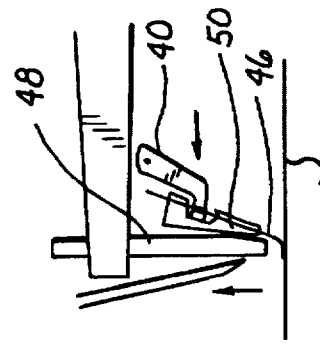
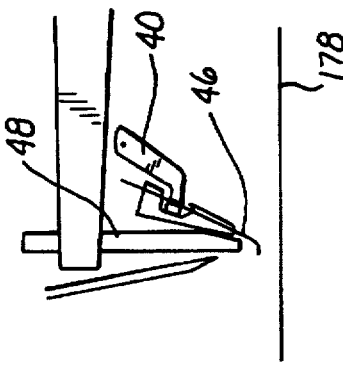
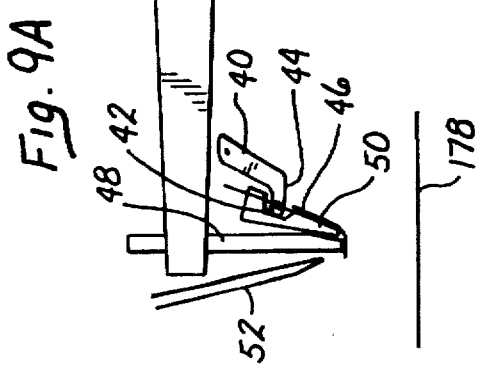

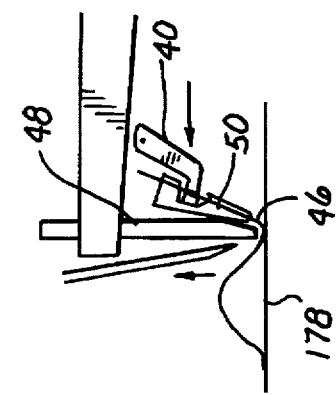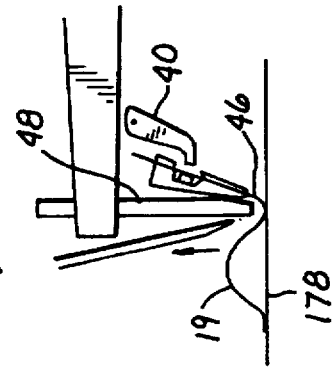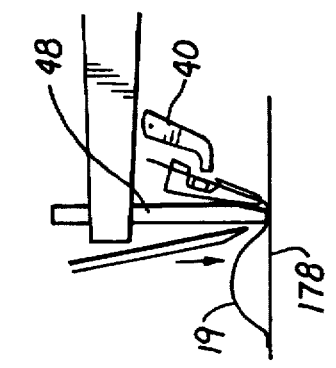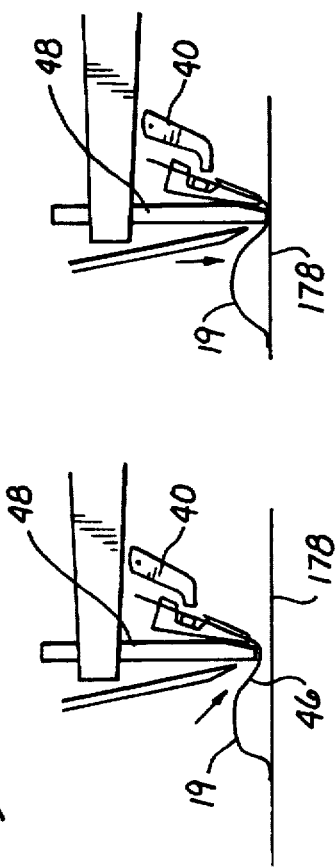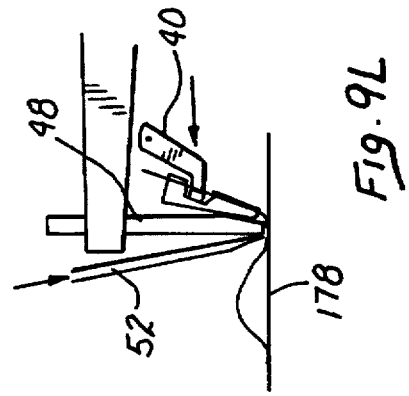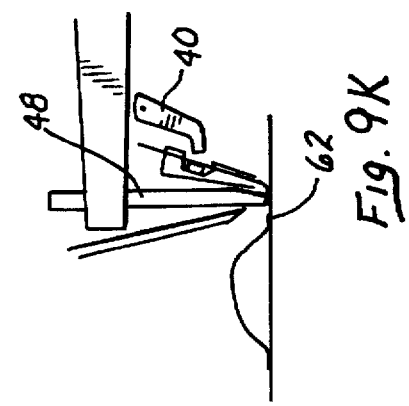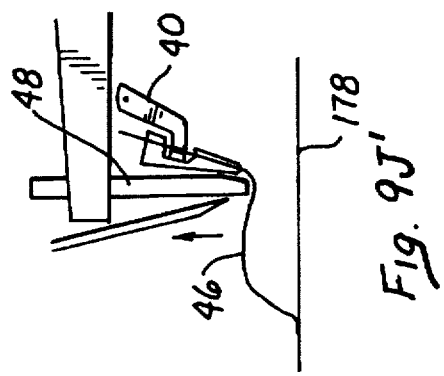

INTEGRATED PULL TESTER WITH AN ULTRASONIC WIRE BONDER

BACKGROUND OF THE INVENTION

1. Field of the Invention

The field of this invention lies within the wire bonding art. It particularly lies within the art of ultrasonic wire bonding as it relates to ultrasonically bonding a wire on such items as electronic circuits and components. The invention is more specifically directed to testing wire bonds through a pull testing system. The pull testing system specifically integrates the process of the pull test with the process of wire bonding.

2. Description of the Prior Art

Prior to this invention the art of pull testing wire bonds was generally done with a pulling device or hook positioned underneath the loop of the bonded wire.

The pulling device or hook lifts up against the wire and places it in tension. This can be seen in FIG. 1 which shows an example of the prior art. The equipment is generally of a type that is stand alone equipment that either functions manually or automatically.

One method of pull testing is by means of a force being applied to the bonded wire loop by a motor driven loading arm. The hook or arm, which is connected to the free end of a flexible cantilever provides a certain force and a strain gauge on the beam measures the deflection. In this manner, the applied pulling force can be indicated by a signal corresponding to the measured force. Further to this extent, the system signifies the distance the hook moves when the strain gauge starts to generate its signal.

Other bonding tests incorporate certain devices to measure the bond's integrity by applying a known and infinitely variable tensile force to the wire under test.

Pull testing when used as a quality check for a bond is generally done in a non-destructive manner. A force is used to stress the bond so as to not cause damage to the wire or the bond. Further pull testing in the prior art can also be done in a destructive manner where the bond is pulled to its failure point. This method is only used on a sample basis since it destroys the bond it is measuring.

The pull force used to non-destructively pull test bonds uses a conventional pulling hook and is limited to a relatively low force. A high force can not be used inasmuch as the hook which is pulling across the axis of the length of the wire imparts a permanent kink, bend, bow or set in the wire. In other words, it bows the wire up, and distorts it from its original relationship as it overlies the circuit, or substrate.

A practical limit to non-destructive pulling forces is within ten to fifteen percent of the yield strength of the wire.

It has been thought that in order to eliminate the bow, the kink, or the angular upward orientation after a pull test is effectuated, the wire should be pulled along its axis. In such a manner, the pull test pulls the wire to a higher level of forces without damaging the wire. This invention enables this pull force along the length of the wire as opposed to across the wire.

Certain patents incorporate devices for testing wire bonds in the entire unit or bond head that moves to and from the bond to be tested. A gauge is incorporated which uses wire grasping hooks operatively connected to the gauge. After grasping a wire in a bonded configuration of a circuit, the gauge is moved away from the support until the wire bond fails and the force is registered by the gauge. In such destructive testing, as well as tests which limit destruction of the bond, substantial complexity of equipment is encountered.

The utilization of pulling hooks is limited in many conditions. The hooks are usually round and have a diameter that is two to three times the diameter of the wire that is to be tested. The hooks can also have a 90° bend forming them into an L shape. These characteristics of the hooks limit them for use on wires that have a very low loop or are not substantially standing away from the surface between which the hooks must engage the wire. Furthermore, the hooks can not be used on wires that are closely bonded together, nor on wires that cross underneath other wires.

The state of the art for pull testing in the semiconductor and the hybrid industries is to use the pull testing as a quality check for the bonding process. It is generally a separate process that is performed after the bonding process is completed. In most cases, there is a significant time span between the bonding and the pull testing. This is not desirable, because in the time it takes to get results from the pull testing, several more rejected parts could be produced by the bonder. Thus, it is desirable to have a system that checks the quality of the bonding as soon as possible after making the bond.

Other methods of checking the quality of wire bonds is to monitor other variables during the bonding process such as the ultrasonic impedance, bond deformation, or frequency shifts. These second order monitoring systems have proven to be valuable in detecting some process variations, but are not as reliable as actually testing the bond through a pull test.

Some ultrasonic wire bonders incorporate a measure of bond quality obtained through non-destructive testing of the bond by developing a voltage proportional to the amplitude of the transverse motion of the ultrasonic bonding tool. The methods develop, by means of a transducer, a second voltage proportional to the tangential component of the forces applied during bonding. The voltages are then fed into a logic circuit to derive their ratio which is a measure of the bonding quality. These methods are not always reliable.

Further bond quality monitoring systems incorporate an analysis of the relative quality of bonding by means of the transducer power signal. In such cases, a series of analog computations based upon the logarithm of the impedance of the transducer is used in order to create a measure of bond quality.

Still other testers incorporate the utilization of a plurality of frequency readings that are taken and measured during the formation of the ultrasonic bond. The information is employed to calculate a bond quality rating, and predicting whether a good bond has been made. This is done by means of providing a signal indicative of a predetermined plurality of cycles from an ultrasonic generator in a stable source of pulses applied to a second counter. Here again, such methods are not deemed to be reliable.

A substantial object of this invention is to overcome the deficiencies of the foregoing prior art.

Another object of this invention is to provide a method and apparatus for pull testing wires that are closely oriented.

A further object is to provide a method of tensile stressing the wire and bond without degrading the bond.

Another object is to provide a fast and inexpensive way to test wire bonds.

Still further, the method and apparatus provides a method of stopping the wire bond process immediately after an inferior bond has been made.

Another object provides a method of testing wire bonds that eventually might become inaccessible by further assembly processes.

Still yet another object is to provide apparatus and a process for testing bonds that have a low loop of wire from the surface that would be incapable of normal conventional bond testing.

A further object is to provide a method of testing bonds that is not influenced by the angle of the wire forming the loop between the bonds.

Yet another object of this invention is to provide a method of pull testing a first bond independent of a second bond.

SUMMARY OF THE INVENTION

In summation, this invention comprises a pull testing method and apparatus for practicing the method as well as unique systems and apparatus for testing ultrasonically bonded wires.

More particularly, the invention comprises a dynamic pull test for wires that have been ultrasonically bonded. The test does not require the utilization of a hook or pulling means that underlies the loop of the wire that is bonded. The invention furthermore provides a wire testing system which does not electronically test the system through transducer forces solely, or other frequency and vibrational modes of the system during a bonding process. Instead, the invention uses the fundamental concept of making a pull test at a given particular pull force to establish whether a bond has been properly made.

In furtherance of the invention, the pull force is directed along the longitudinal axis of the wire. This serves to allow for a stronger pull force without bowing, kinking or angularly deforming the wire in the middle or looped portion.

Further to this invention, is the fact that the pulling forces established for testing the wire do not have to be undertaken by hooking, interconnecting, or mechanically in any manner drawing the wire away from the surface at its bowed or looped area. This eliminates the requirement of testing wires that have sufficient space between them to allow emplacement of a hook or an L shaped angle member. Consequently, such wires that have been emplaced closely, cross looped, or are in tight adjacent relationship, or those which have very low lying loops can be tested by this method and apparatus.

For this reason, it is believed that this invention is a substantial step over the prior art in testing ultrasonically bonded wires.

BRIEF DESCRIPTION OF THE DRAWINGS

FIG. 1 is a perspective view of the prior art.

FIG. 2 is a fragmented side elevation view of a small wire bonder of this invention.

FIG. 2A shows a fragmented side elevation view of a large wire bonder of this invention.

FIG. 2B shows a cross-sectional view in the direction of lines 2B of FIG. 2.

FIG. 3 shows a schematic view of a portion of the bonding head this invention.

FIGS. 6A through 6J show a series of articulated movements of the wire bonder of this invention through the various bonding, clamping, lifting, and pull testing steps for the small wire bonder of FIG. 2.

FIGS. 9A through 9L show a large wire bonding series of steps for effectuating a bond and an accompanying pull test.

DESCRIPTION OF THE PREFERRED EMBODIMENTS

Figure 4:
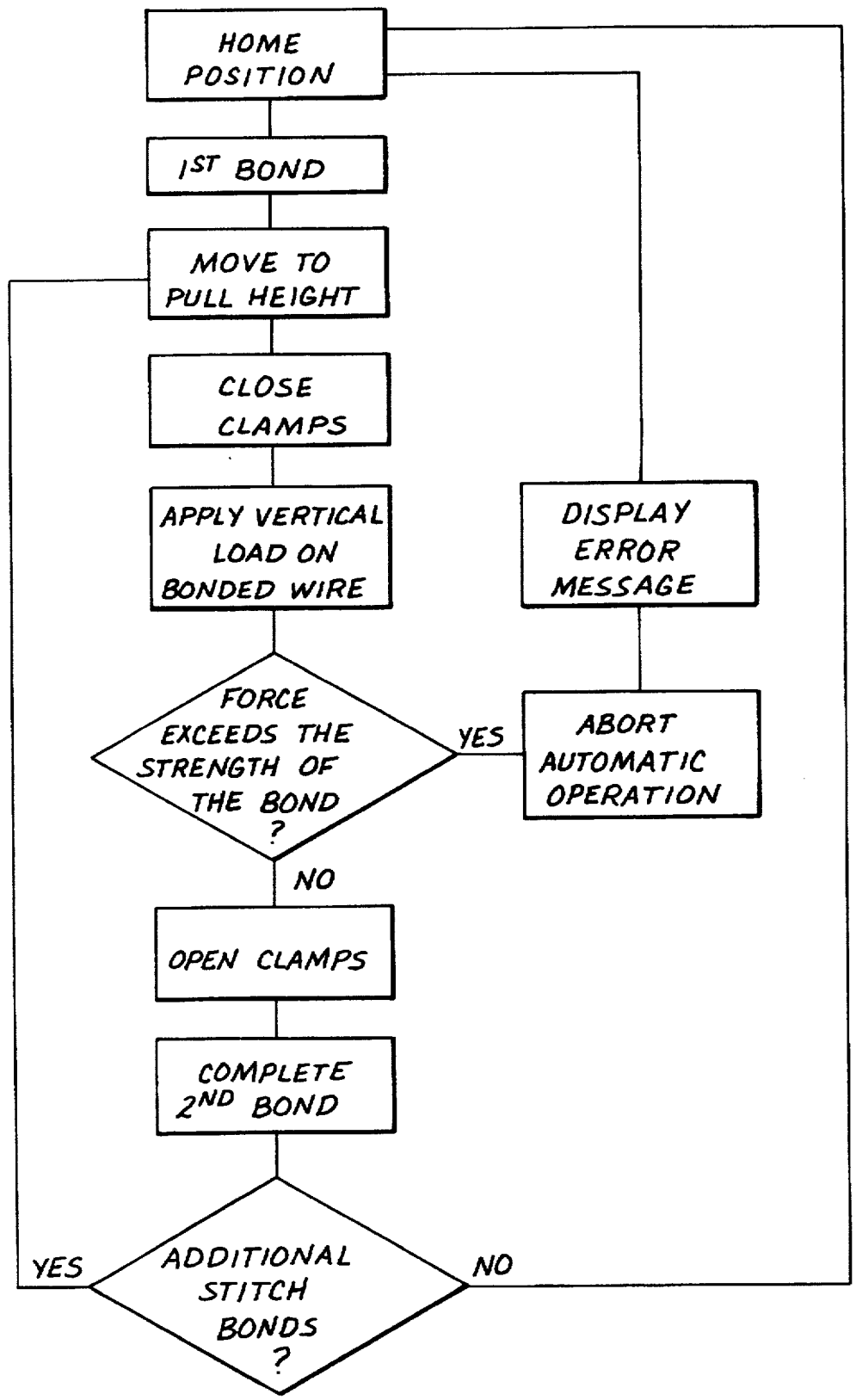
FIG. 4 shows a block diagram of the logic of the small wire bonding method of this invention.

As previously stated with respect to the prior art, pull tests generally function with a hook or L shaped member pulling the bonded wire. As can be seen in FIG. 1, a wire 10 that has been ultrasonically bonded with bonds 12 and 14 has a loop portion 16. The loop portion 16 is of sufficient height to allow an L shaped member 18 to pull the loop 16. This upward force in the direction of arrow 20 tends to bow or loop the wire 10 further to a point where it sticks up with a higher profile than is desirable. Also, it can stress the bonded wire to the point where it creates an angular or offset portion in the bowed section 16.

FIG. 2 shows a wire 22 that is being held by a wire clamp 24. The wire 22 and the wire clamp 24 are shown with a bonding tool 26. The wire clamp 24 comprises two jaws 28 and 30 that hold the wire 22 therein. In order to properly feed the wire, a tapered opening, aperture or hole 32 passes through the bonding tool 26. It can be seen that the bonding tool 26 is moving upwardly in the Z direction of the arrow in a manner that will be detailed further hereinafter.

In order to allow the passage of the wire 22, a stepped angular portion 36 is included to provide for relief and passage of the wire 22. The clamping of the wire can further be seen in the cross-sectional showing of FIG. 2B wherein the wire 22 is shown clamped between the two jaws 28 and 30. The foregoing wire clamp and bonding tool of FIGS. 2 and 2B are generally utilized for wire sizes which are categorized as small wire in the nature of 0.003 inches or less in diameter. Also it should be understood that the showings of FIGS. 2 and 2B are relatively simplified.

The elements of FIGS. 2 and 2B are attached to a bonding head of significant complexity that causes the tool 26 and clamp 24 to move in X, Y and Z directions. The X and Y directions are generally planar, with the substrate to which a bond is being made. The Z directional moves cause the head with the tool 26 and clamp 24 to move upwardly and downwardly.

FIG. 2A shows a clamp 40 having jaws 42 and 44. The jaws are shown clamping a heavier aluminum wire 46. The heavier wire is referred to as large wire in the bonding art and is usually greater than 0.003 inches in diameter. FIG. 2A shows a bonding tool 48 moving upwardly in the direction of arrow Z with an adjacent wire guide 50 which is also moving upwardly simultaneously. The wire guide 50 moves in conjunction with the bonding tool which is necessary to make the bond. This is generally controlled by the bonding head to which the tool 48 and clamp 40 are attached to.

The bonding tool 48 operates in conjunction with a cutter 52 having a cutter blade knife like edge 54 for cutting the wire after it has been bonded.

Figure 7:
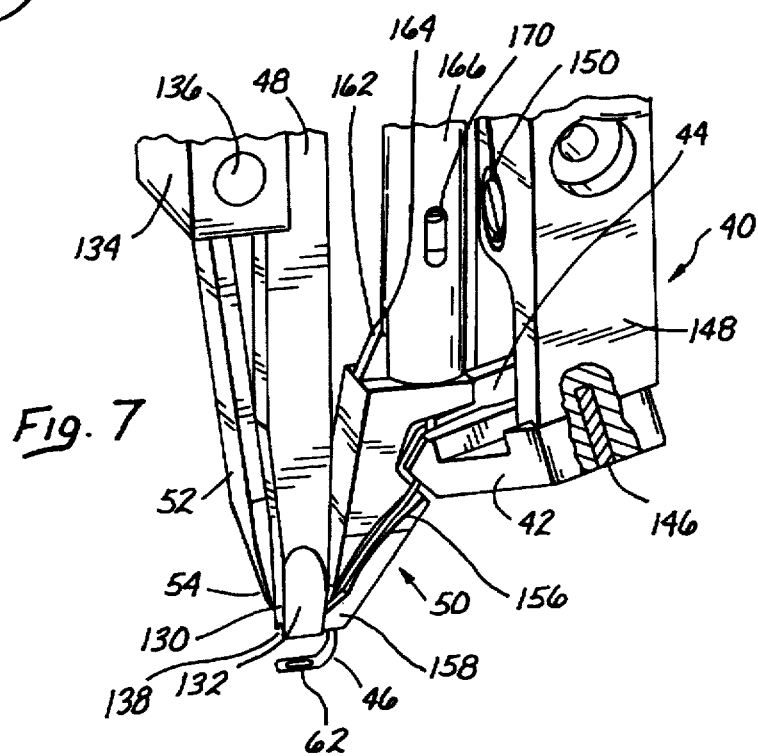
FIG. 7 shows a perspective view of a portion of a large wire bonding head and clamps analogous to that shown in FIG. 2A, but in greater detail.

The bonding tool 48 does not require a feed aperture or tapped hole, but has a groove 138 in its base as seen in FIG. 7.

Both FIGS. 2 and 2A show bonds respectively at bonding points 60 and 62 that have been made by the foot or lower portion of the bonding tools respectively 26 and 48. These bonds are accomplished by the respective bonding tools 26 and 48 being ultrasonically vibrated by a transducer which has been shown in FIG. 3. For further reference with regard to the operation of the bonding tools and clamps and their respective functions when attached to a bonding head reference can be had to U.S. Pat. No. 4,976,392 as well as U.S. patent application Ser. No. 08/615,470 which are owned by the same assignee herein.

When looking at FIG. 3, it can be seen that a transducer 66 is shown with a cartridge portion 68. The cartridge portion 68 is connected to a horn 70 to propagate the ultrasonic vibratory modes from the cartridge forming the transducer to the bonding tool which in this case is the small wire bonding tool 26 of FIG. 2.

The transducer with the cartridge 68, horn 70, and bonding tool 26 pivot upwardly and downwardly on a pivot point 74 mounted on a block 76. This portion of the bonding head can also be seen in the foregoing referenced patents and application.

In order to provide control, movement, and force on the bonding tool 26, a forcer mechanism in the form of a magnet having north and south portions N and S respectively is controlled by a coil 80 that is driven by a force controller 82. As the bonding tool 26 pivots upwardly and downwardly the force can be adjusted.

A position sensor 86 is shown that positions the bonding tool 26 as it pivots around pivot point 74. The control is through a linear variable differential transducer, described in the foregoing U.S. patent application Ser. No. 08/615,470. For purposes of explanation, it is merely seen as two members that move in relationship to each other for purposes of determining the position of the horn 70 and the attendant attached bonding head 26. The linear variable differential transducer, has been shown as two plates that move respect to each other, namely plates 87 and 88 which comprise the linear variable differential transducer 90. The entire movement is controlled by a central processor 94 which activates the movement through the forcer mechanism 80 as controlled by the force controller 82.

The linear variable differential transducer 90 can be substituted by a capacitance sensor, a HALL effect sensor, optical sensors, or linear encoders to determine the position of the horn 70 and the attendant bonding tool 26.

In order to control the wire 22 it is shown being fed from a spool 96, the clamp jaws of the clamp 24 are shown in diagrammatic form as jaws 28 and 30. These serve to clamp the wire 22 in the analogous manner of the showing of FIG. 2 and for purposes of explanation in an analogous manner to that of FIG. 2A except for the various features as will be detailed in FIGS. 7 and 9A through 9L.

In order to perform a bond, the bonding tool 26 moves downwardly onto the wire 22 and is vibrated ultrasonically by the transducer 66 propagating ultrasonic energy through the horn 70 to the bonding tool 26 so that an underlying semiconductor has the wire 22 bonded to it.

In order for there to be an understanding of the small wire bonding of FIGS. 2, 2B, 3 and 6A through 6J, a review of FIGS. 6A through 6J is hereinafter set forth.

In FIGS. 6A through 6J, a substrate 102 has been shown in each of the Figures. This substrate 102 can be in the form of a semiconductor circuit or any other suitable electronic component.

Figure 6A:
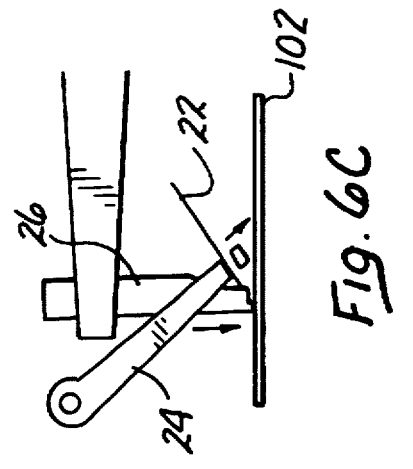

The substrate 102 to which the wire 22 is to be bonded can be seen starting in FIG. 6A wherein the bonding tool 26 and the entire wire bonding head is in the home position. The wire is clamped between jaws 28 and 30. In clamping the wire between jaws 28 and 30, it can be seen that the wire is confined and must move with the respective bonding head. Please also note that the showing of FIGS. 6A through 6J is for purposes of example and the clamp 24 and jaws 28 and 30 are analogous, though not identically oriented to those of FIG. 2.

Figure 6B:
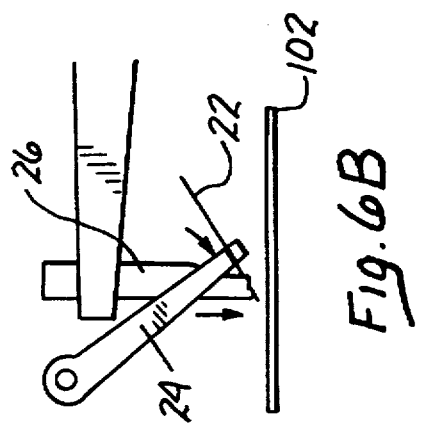

FIG. 6B shows the bonding tool 26 with the wire 22 held in the clamp jaws of the clamp 24 moving downwardly in the direction of the arrows. As the bond head moves downwardly with the tool 26, it has the wire held by the jaws 24 in close juxtaposition to the end of the bonding tool 26.

Figure 6C:
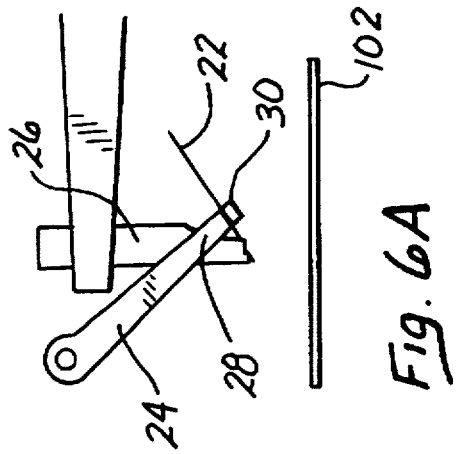

FIG. 6C shows the clamp 24 opening up and the bonding tool 26 moving downwardly further in order to make a bond against the substrate 102. The clamp 24 is open at this point for purposes of allowing the wire to feed out to start making the loop 17.

Figure 6E:
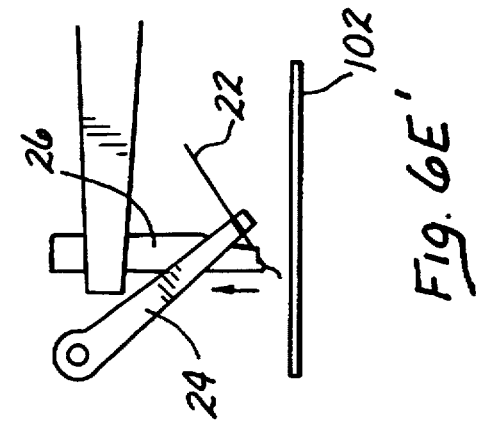
Figure 6E:
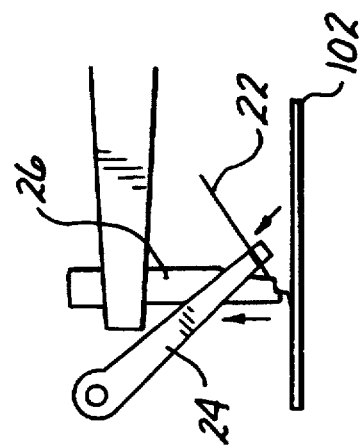
Figure 6D:
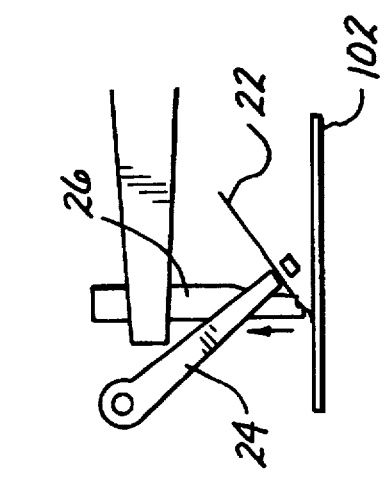

FIG. 6D shows the bonding tool 26 lifting away with the clamp 24 in adjacent relationship thereto. When lifting off the surface to the proper height, the clamp 24 is still open to allow slight movement of the wire 22 to form a proper loop and allow the bonding head 26 with the clamp to move away from the bond.

In FIG. 6E, the clamp 24 is closed. When the clamp is closed, at an appropriate pull height which has been established, a pulling force against the bonded wire is effected under a programmable amount of force. This pulling in the axial direction of the wire allows a test of the first bond that has been formed in the showing of FIG. 6C. If the wire does not move from the surface and is relatively static, taking into consideration a programmable amount of stretch or movement due to orientation of the wire, a good bond has been established. In effect the lack of movement of the tool 26 and the clamp 24 in its closed position when lifting or pivoting the bond head establishes the bond is firm fixed and in place. Pulling of the wire by the bond head movement with the clamp 24 closed without the wire moving establishes that the bond is fixed.

Looking at FIG. 6E', it can be seen that the bonding tool 26 and clamp 24 has moved upwardly in the test of FIG. 6E. The wire 22 has become disassociated as can be seen in the gap between the substrate 102 and the tail or end of the wire. The force applied during the test of FIG. 6E has pulled the wire 22 away from the surface 102, and is indicative of a bad bond. The entire process is then stopped from the standpoint of bonding so that operator intervention or other automatic activity can take place to provide for continued bonding.

FIG. 6F shows the bonding tool 26 with the clamp 24 and wire 22 moving upwardly from the surface 102. At this point, the clamp 24 has been opened and provides for a looped formation of the wire 22.

FIG. 6G shows the bonding tool 26 and the clamp 24 moving downwardly with the wire 22 to provide for a second bond. The second bond placement provides for the loop shown as loop 17 of the wire analogous to the loop 16 shown in the prior art. This loop has been established by the movement of the bonding tool and clamp 24 to a preprogrammed area which is the proper location for a second bond.

FIG. 6H shows the wire 22 that is being bonded with the clamp 24 with the jaws 28 and 30 opened. However in some instances it has been found that the clamp 24 can be closed at this point.

Looking at FIG. 6I, it can be seen that the bonding tool 26 has bonded the wire to the substrate as can be seen in detail in FIG. 6I', and the clamp 24 is rotating in the direction of the arrows with the clamp jaws closed. This serves to break the wire as seen detailed in FIG. 6I'. The wire has now been broken and the bonding tool 26 with the wire and the clamp 24 is shown moving upwardly so that the wire 22 can be prepared for another bond in the home position of 6J analogous to FIG. 6A.

In order to provide a detail of a portion of the large wire bonding head, a perspective view is shown in FIG. 7. This portion of the bonding head has a bonding tool 48 with a chamfered surface 130 on the front and back and a chamfered surface 132 on either side. These chamfered surfaces allow for a more specific centering of the tool 48 over the wire 46 that is to be bonded. The cutter blade 52 is shown having a knife edge 54 and is held by a mounting block 134 with a tightening screw mount 136.

The wire 46 is shown bonded at a bonding point 62 by ultrasonic bonding. In order to impress the wire 46 against the bonding tool 48, a groove 138 is formed within the bottom of the bonding tool.

The jaws of the clamp analogous to FIG. 2A and those of FIGS. 9A through 9L have been shown in greater detail. The showing of FIG. 7 includes the clamp 40 with jaws 42 and 44. These jaws 42 and 44 are secured by screws 146 shown in fragmented cross-section, each threaded into a clamp arm 148. Clamp arms 148 pivot on a spring loaded pivot point 150. The clamp arms 148 are symmetrical on either side, so that jaw 44 analogous to jaw 42 opens and closes in a clamping manner.

In order to guide the wire 46 into position under the bonding tool 48, the wire guide 50 is shown having a slot 156 through which the wire passes. A pair of shoulders 158 allow the wire to pass therethrough and allow emplacement of the wire to a position under the bonding tool 48 and in particular the slot or groove 138.

The wire guide 50 extends upwardly and terminates in an alignment key 162 that is emplaced within a slot 164 of a wire guide tube 166. The wire guide tube 166 has a locking detent 170 so as to allow retention and placement in proper alignment.

Looking more particularly at FIGS. 9A through 9L the bonding tool 48 is shown in adjacent relationship to the cutter blade 52. In conjunction therewith, the wire 46 is shown passing with respect to the clamp 40 and the wire guide 50. A substrate analogous to the prior substrate 102 shown in the FIGS. 6A, etc. has been shown as a substrate 178. The jaws 42 and 44 of the clamp 40 are shown for illustration purposes only in a slightly different orientation to that of the showing of FIG. 7.

The FIGS. 9A through 9L are for heavy wire bonding with the cutter blade 52. The showing in FIG. 9A is of the bonding tool 48 and head in the home position.

FIG. 9B shows the bonding tool moving toward the bond position over the substrate 178 on which to provide for a wire bond. The tool 48 is moving downwardly with the bonding head and the wire 46 is shown within the groove that has been detailed as groove 138 in the portion shown of the bonding head of FIG. 7.

In FIG. 9C, bonding is taking place and the clamp 40 is opened.

In FIG. 9D, the bonding head is being lifted off with the clamp 40 opened so as to release the wire 46 that has been bonded to the substrate 178. The bonding head in FIG. 9D is moving up to a height at which the pull height is established for pulling and testing the bond.

In FIG. 9E, the bonding tool 48 and the head have been lifted up with the clamp 40 closed. This is in the vertical or Z direction. With the clamp 40 closed, the wire 46 is then pulled for testing purposes. In order to establish the proper pull, a certain degree of stretch is preprogrammed into the pull test to take into consideration the slight stretch and movement of the wire, with regard to the substrate 178.

FIG. 9F shows the fact that a good bond has taken place on the substrate 178. The bonding head with the tool 48 is moved upwardly with the clamp 40 open to provide for a looped movement of the wire. At this point, it can also be seen that the clamp 40 by releasing the wire allows for this looped movement as the head moves in the Z, and the X and/or Y directions.

FIG. 9E' shows the fact that a bad bond has taken place by the wire 46 parting from the substrate 178. The wire 46 has been pulled and fractured with respect to its bond, or the bond was never successful to any degree at all. The parted bond is the outgrowth of the operation in FIG. 9E with the movement upwardly in the Z direction and the clamp 40 closed. The failure of the bond is then recorded and the equipment can then be stopped in order to reject the part and move on to continuous bonding of other parts.

Assuming the bond has been successful as in FIG. 9F after the test of FIG. 9E, the bonding tool 48 moves downwardly to complete the loop. The loop is that loop which is generally shown as loop 19 analogous to loop, 17 and loop 16 shown in the prior art. The clamp 40 is open, and the feeding of the wire 46 downwardly places the wire in a position to be bonded by the bonding tool 48.

In FIG. 9H, it can be seen that the bonding tool 48 has touched the substrate 178 and bonding is taking place.

In FIG. 9I the head with the bond tool 48 and the clamp 40 moves up to the pull height with the clamp open.

In FIG. 9J, the bonding head is moved upwardly with the clamp 40 closed in order to pull test the wire 46 while it is still in the wire guide 50. The pull test at this particular portion attempts to part the wire 46 from the substrate 178. The clamp being closed and the pull test being undertaken causes either a successful pull so that the wire does not part from the substrate, or the wire pulls away as seen in FIG. 9J'. FIG. 9J' shows the bonding head moving away with the clamp 40 closed and the wire 46 moving away from the substrate 178. At this point, the wire bonder is then stopped and the part rejected.

Assuming the pull test of FIG. 9J is successful, the bonding head with the bonding tool 48 then moves in the manner shown in FIG. 9K. During this movement, the jaws 42 and 44 of clamp 40 are opened so as to allow the bonding head with the bonding tool 48 to move upwardly and downwardly in an arcuate motion. This moves the bonding tool 48 with the wire backwardly from the bond 62 which is shown having been successfully bonded. Thereafter, the cutter block 134 moves the cutter blade 52 downwardly as shown in FIG. 9L in order to sever the wire. The clamp is closed in order to maintain the position of the wire and provide for proper cutting without disorientation.

The logic of the small wire bonding shown in FIGS. 6A through 6J can be seen in FIG. 4. The bonder starts at the home position afterwhich a first bond is made and the head then moves to the pull height. The clamps are then closed and a vertical force is applied to the bonded wire.

Thereafter, if the force exceeds the strength of the bond causing the bond to fail, the bonding sequence is aborted. A display error message is then provided, or mechanical means are implemented in order to stop the motion of the bonder and provide for the failure to be indicated and appropriate action taken.

Assuming that the force did not exceed the strength of the bond and the bond remains intact, the clamps are then opened and a completed second bond is made. If there are additional stitch bonds which are multiple bonds along the length of the same wire, the process proceeds in a manner whereby the bonding head and tests continue on with the pull height and closing of the clamps after each bond. If there are no additional stitch bonds, the head with the bonding tool moves back to the home position and small wire bonding continues. The analogous, though not identical, logic functions are also true with regard to the logic applied in the steps of FIGS. 9A through 9L for large wire bonding.

Figure 5:
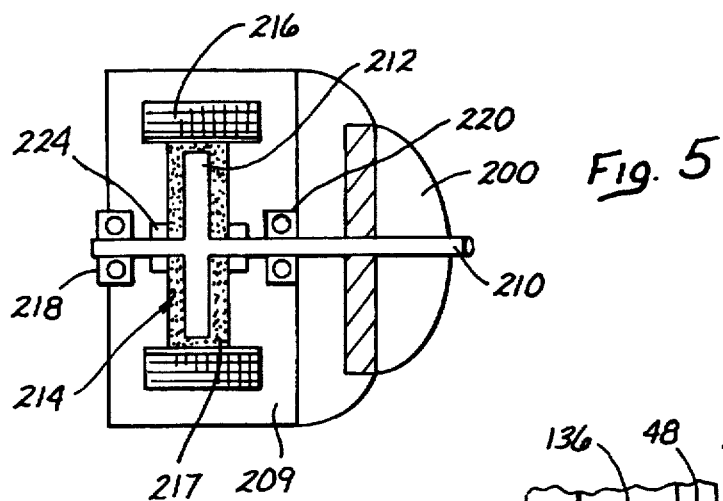
FIG. 5 shows an alternative embodiment of this invention in cross-section as to its clutching mechanism as taken in a mid-line cross-section of the hub 200 shown in FIG. 8.
Figure 8:
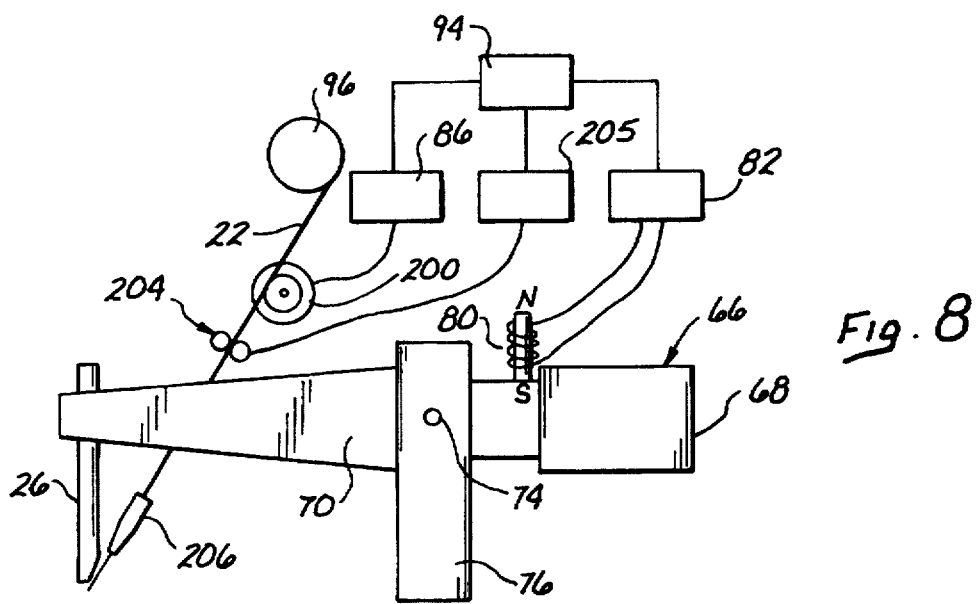
FIG. 8 shows an alternative embodiment of a system for testing a bond utilizing a frictional engagement or clutched handling of wire rather than a direct pull test.

Looking more particularly at FIGS. 5 and 8 the bonding head is the same, but for a hub 200 that applies torque or a pull force to the wire 22 being fed from the wire spool 96. The hub 200 controls the wire from the standpoint of the amount of pull force that can be applied to the wire 22.

In association with the system is an encoder 204 through which the wire 22 passes. The encoder 204 monitors how much wire is being fed out. The encoder 204, when the bonding tool 26 with the entire head moves upwardly, determines whether or not there is a good bond. In effect, if the encoder does not detect any feed out of wire 22 when the bond head moves upwardly, then the bonded wire has been lifted off the surface through the wire guide such as the wire guide 206.

A type of friction brake that can be utilized has been shown in FIG. 5 with the hub 200 allowing the wire to pass thereover. The hub 200 is connected to an output shaft 210 mounted in a housing 209 that is in turn connected to a disk 212. The disk 212 is within a multiplicity of magnetic particles 217 in a chamber 214. An electrical coil 216 is shown surrounding the chamber 214. Bearings 218 and 220 are shown on either side for supporting the shaft. Seals 224 are shown sealing the shaft 210 mounted in the housing 209 to allow for rotation in sealed relationship without disturbing the magnetic particles.

The output disk 212 attached to the shaft 210 does not touch the housing 209. The magnetic particles in the chamber 214 are fine stainless steel powder particles that are free flowing until a magnetic field is applied from the coil 216. The particles form chains along the magnetic flux lines linking the disk 212 to the housing 209. The torque is proportional to the magnetic field which is dependent upon the dc input current. This input current can be established through the position sensor 86 providing a dc current to the coils 216 to provide for the braking or torque applied to the disk 200.

This allows the output of the position sensor 86 to create sufficient torque so that when the bonding head including the bonding tool and wire 22 are lifted up after a bond, a given amount of force against the wire permits the pull test to be performed. The encoder 204 has its output recorded in an encoder recorder 205 that effectively is connected to the position sensor and control processor 94. This enables a determination of whether a good bond has been made when the head lifts by virtue of the encoder either not moving which indicates a bad bond, or slight movement of the wire which shows it is being paid out by virtue of the head moving upwardly while the bond remains on the substrate.

Other types of hubs can be used, or controlled clutches, such as friction clutches, slip torque brakes, brakes or other such types which allow for a proportional amount of force to be applied against the wire upon lifting. Tensioning of any type can be effectuated with the torque of the hub 200 or other slip or cog means.

From the foregoing, it can be seen an alternative pull test has been established with the disclosure of the friction hub or brake 200.

It should be understood that other alternative embodiments in the scope of the claims can be utilized to effect the pull test of this invention and accordingly the claims should be read broadly in light of the foregoing specification.

I claim:

1. A method for forming and testing a bond by an ultrasonic wire bonding tool comprising:

placing a wire that is to be bonded into overlying relationship to a substrate that it is to be bonded to;

placing a bonding tool in contacting relationship with said wire;

ultrasonically driving said bonding tool sufficiently to create a bond; and, pulling said wire with a drag force applied by a rotational brake to which said wire is in contact with substantially in the direction of the longitudinal axis of said wire sufficiently to determine the strength of said bond.

2. The method as claimed in claim 1 further comprising:

guiding said wire by a guiding means.

3. The method as claimed in claim 1 further comprising:

holding said wire by a clamp having jaws which secure said wire.

4. The method as claimed in claim 3 further comprising:

moving said wire with respect to said substrate by said clamp.

5. The method as claimed in claim 1 further comprising:

severing said wire by means of a cutter blade in proximate relationship to said wire bonding tool.

6. The method as claimed in claim 4 further comprising:

severing said wire after a bond has been made by said clamp holding said wire and pulling it from said bonded portion at sufficient strength to sever said wire.

7. The method of testing a bond as claimed in claim 1 further comprising:

retarding the movement of said wire by said drag force while lifting the wire in relationship to said bond to establish a pull on said bond of a force sufficient to test the pre-established desired strength of the bond.

8. The method as claimed in claim 7 further comprising:

encoding movement of said wire while it is being retarded to determine whether the wire has moved from its bonded relationship to a substrate.

9. An ultrasonic wire bonding method and method for testing the bond comprising:

providing a bonding tool adapted to be ultrasonically driven for ultrasonically bonding a wire on an underlying substrate;

holding wire to be bonded by said bonding tool;

rotationally supporting said wire so that wire passing over said support rotates said support; and, retarding said support after wire has been bonded with a retarding force to determine whether the bond will withstand said force.

10. The method as claimed in claim 9 further comprising:

pulling the wire that has been bonded after the last bond has been completed for purposes of severing the wire beyond the last bond.

11. The method as claimed in claim 9 further comprising:

cutting the wire after a bond.

12. The method as claimed in claim 10 further comprising:

guiding wire that is to be bonded by said bonding tool.

13. The method as claimed in claim 11 further comprising:

guiding wire to the bonding tool; and, providing a groove underlying said bonding tool for receiving a portion of the wire that is to be bonded.

14. The method as claimed in claim 9 further comprising:

ultrasonically driving the bonding tool connected thereto;

pivoting said bonding tool with respect to a substrate upon which a wire bond is to take place;

sensing the position of said bonding tool;

controlling the force on said bonding tool; and, linking a control processor while position sensing for providing a pre-determined force based upon the position of said bonding tool.

15. The method as claimed in claim 9 further comprising:

causing said bonding tool while said wire is being held to move in at least two out of three of the directions of the X, Y and Z directions with respect to a substrate to which a bond has been made for forming a loop between the first bond and a second bond.

16. The method as claimed in claim 9 further comprising:

restricting further bonds after a bond has been pulled away from a substrate by the force of said retarding movement by said rotational support.

17. A method of wire bonding including a wire bonding tool, and means for guiding wire to the bonding tool wherein the improvement comprises:

applying a drag force to said wire by a rotational support to which said wire is in contact with after said wire has been bonded as the bonding head to which the bonding tool is attached is raised.

18. The method as claimed in claim 17 further comprising:

applying said drag force by a rotational brake over which said wire passes that applies a pre-established retarding force on the wire as said wire is paid out with respect to said brake.

19. The method as claimed in claim 17 wherein;

said drag force is provided by an electrical brake having a disk in contacting relationship to said wire that has been connected to a rotary disk incorporated within a field which applies a magnetic drag to said disk.

20. The method as claimed in claim 19 wherein:

said rotary disk is within a chamber filled with particles of magnetically orientable material that are oriented by coil means to provide a rotary drag on the disk proportional to the current on said coil means.

21. The method as claimed in claim 17 further comprising:

establishing movement of the wire by an encoder through which the wire passes.

22. An ultrasonic wire bonding method comprising:

providing a bonding tool;

ultrasonically driving said bonding tool by a transducer means connected to said bonding tool;

holding wire that is to be bonded in a fixed position in part by a rotational support; and, moving said rotational support upwardly after a bond has been formed while retarding rotation thereof to pull said wire at a pre-established force for determining the strength of the bond by an encoder.

23. The method as claimed in claim 22 further comprising:

rotationally retarding said rotational support by magnetic means.

24. The method as claimed in claim 22 further comprising:

a cutting tool adjacent said bonding tool for cutting a wire that has been bonded by a tool adjacent said bonding tool.

\* \* \* \* \*